(12) United States Patent
Kim et al.

(10) Patent No.: US 9,841,415 B2
(45) Date of Patent: Dec. 12, 2017

(54) NONINVASIVE APPARATUS AND METHOD FOR TESTING GLYCATED HEMOGLOBIN

(71) Applicant: SAMSUNG ELECTRONICS CO., LTD., Suwon-si (KR)

(72) Inventors: Sangkyu Kim, Yongin-si (KR); Joonhyung Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 126 days.

(21) Appl. No.: 14/825,302

(22) Filed: Aug. 13, 2015

(65) Prior Publication Data

US 2016/0061810 A1 Mar. 3, 2016

(30) Foreign Application Priority Data

Sep. 3, 2014 (KR) .................. 10-2014-0117025

(51) Int. Cl.
*G01N 33/49* (2006.01)
*G01N 21/552* (2014.01)
(Continued)

(52) U.S. Cl.
CPC ........... *G01N 33/49* (2013.01); *A61B 5/0075* (2013.01); *A61B 5/1455* (2013.01); *A61B 5/14532* (2013.01); *G01N 21/552* (2013.01); *A61B 5/7246* (2013.01); *G01N 21/65* (2013.01); *G01N 2021/3595* (2013.01)

(58) Field of Classification Search
CPC .... G01N 33/49; G01N 21/552; A61B 5/0075; A61B 5/14532; A61B 5/1455
See application file for complete search history.

(56) References Cited

U.S. PATENT DOCUMENTS 4,169,676 A * 10/1979 Kaiser .................. G01N 21/552
356/39
6,949,070 B2 9/2005 Ishler
(Continued)

FOREIGN PATENT DOCUMENTS

JP 2002-202258 A 7/2002
KR 10-0694598 B1 3/2007
KR 10-2010-0022614 A 3/2010

OTHER PUBLICATIONS

Ishan Barman, et al., "Raman Spectroscopy-Based Sensitive and Specific Detection of Glycated Hemoglobin", Analytical Chemistry, American Chemical Society, Feb. 12, 2012, 84, pp. 2474-2482.

*Primary Examiner* — David Porta
*Assistant Examiner* — Mindy Vu
(74) *Attorney, Agent, or Firm* — Sughrue Mion, PLLC

(57) ABSTRACT

An apparatus for testing glycated hemoglobin includes a first light measurement device configured to radiate a first light to an object and detect first information about the first light reflected from the object, a second light measurement device configured to radiate a second light to the object and detect second information about the second light reflected from the object, a data extractor configured to extract first extracted data related to hemoglobin from the first information and second extracted data related to glucose from the second information, and a data processor configured to determine information related to glycated hemoglobin from the first extracted data and the second extracted data.

23 Claims, 6 Drawing Sheets

(51) Int. Cl.
*A61B 5/00* (2006.01)
*A61B 5/145* (2006.01)
*A61B 5/1455* (2006.01)
*G01N 21/65* (2006.01)
*G01N 21/35* (2014.01)

(56) References Cited

U.S. PATENT DOCUMENTS

| | | | | |
|---|---|---|---|---|
| 7,725,144 | B2* | 5/2010 | Ediger | A61B 5/0059 |
| | | | | 356/301 |
| 9,429,579 | B2* | 8/2016 | Sugiyama | G01N 33/66 |
| 2006/0195022 | A1 | 8/2006 | Trepagnier et al. | |
| 2010/0298675 | A1* | 11/2010 | Al-Ali | A61B 5/14551 |
| | | | | 600/322 |
| 2011/0238324 | A1* | 9/2011 | Matsushima | A61B 5/117 |
| | | | | 702/19 |
| 2013/0261413 | A1* | 10/2013 | Kawahara | A61B 5/1455 |
| | | | | 600/316 |

* cited by examiner

NONINVASIVE APPARATUS AND METHOD FOR TESTING GLYCATED HEMOGLOBIN

RELATED APPLICATIONS

This application claims priority from Korean Patent Application No. 10-2014-0117025, filed on Sep. 3, 2014 in the Korean Intellectual Property Office, the disclosure of which is incorporated herein in its entirety by reference.

BACKGROUND

1. Field

Apparatuses and methods consistent with exemplary embodiments relate to testing glycated hemoglobin in a noninvasive manner.

2. Description of the Related Art

The average life expectancy has gradually increased due to development of medical science. The increase in the average life expectancy has been affected not only by the development of medical science, but also by an increase in the public's interest in health and a growing interest in the management of personal health.

As many personal medical apparatus which allow individuals to check their own health have been developed, people may be able to check on their health without visiting hospitals. Adult diseases which may be monitored by an individual include cerebrovascular disease, hypertensive disease, diabetes, liver disease, etc. For example, automatic sphygmomanometers are available at many places such as public buildings. As a further example, in order to check for liver disease, blood is sampled to measure a liver function index. As another example, many diabetes patients frequently check their blood sugar by using a compact blood sugar tester without visiting hospitals. Diabetes is a group of metabolic diseases in which the person has high blood glucose (blood sugar), either because insulin production is inadequate, or because the body's cells do not respond properly to insulin, or both. Patients with high blood sugar may release glucose through urine. Diabetes patients may check blood sugar levels several times a day to ensure adequate levels of insulin. However, it is painful to sample blood, and drawing blood samples regularly may create a psychological burden. Also, since frequent blood sampling may be harmful to a person, it may be difficult to frequently administer blood sugar tests.

SUMMARY

One or more exemplary embodiments provide an apparatus for testing glycated hemoglobin in a noninvasive manner and display an output of the test.

One or more exemplary embodiments also provide a method for testing glycated hemoglobin in a noninvasive manner.

According to an aspect of an exemplary embodiment, there is provided an apparatus for testing glycated hemoglobin, the apparatus including a first light measurement device configured to radiate a first light to an object and detect first information about the first light reflected from the object, a second light measurement device configured to radiate a second light to the object and detect second information about the second light reflected from the object, a data extractor configured to extract first extracted data related to hemoglobin from the first information and second extracted data related to glucose from the second information, and a data processor configured to determine information related to a concentration of glycated hemoglobin in the object from the first extracted data and the second extracted data.

The apparatus may further include a display configured to output the information related to the concentration of glycated hemoglobin as a result of a test performed on the object.

The data extractor may be further configured to determine a ratio of the second extracted data to the first extracted data.

The data processor may be further configured to determine a ratio of the glycated hemoglobin to the hemoglobin from the first extracted data and the second extracted data.

The first light may include visible light or near-infrared light and the second light includes a laser light.

The first light measurement device may include an absorption spectrophotometer and the second light measurement device may include a Raman spectrophotometer.

The first light measurement device may include a Fourier transform infrared spectrometer.

The first light measurement device and the second light measurement device may further include an attenuated total reflectance prism.

The data processor may be further configured to determine information about a correlation of a ratio of the first extracted data and the second extracted data and a ratio of the glycated hemoglobin to the hemoglobin.

The information about the correlation may include a correlation equation or a lookup table.

The data extractor may be further configured to extract data of light intensity with respect to a wave number corresponding to the hemoglobin in an absorption spectrum of the first light reflected from the object, and data of Raman light intensity with respect to a wave number corresponding to the glucose in an absorption spectrum of the second light reflected from the object.

According to an aspect of another exemplary embodiment, there is provided a method for testing glycated hemoglobin, the method including radiating a first light to an object, radiating a second light to the object, detecting first information about the first light reflected from the object, detecting second information about the second light reflected from the object, extracting first extracted data related to hemoglobin from the first information, extracting second extracted data related to glucose from the second information, and determining information related to a concentration of glycated hemoglobin in the object from the first extracted data and the second extracted data.

The method may further include displaying the information related to the concentration of glycated hemoglobin as a result of a test performed on the object.

The method may further include determining a ratio of the second extracted data to the first extracted data.

The determining of the information related to glycated hemoglobin may include determining a ratio of the glycated hemoglobin to the hemoglobin from the first extracted data and the second extracted data.

The first light may include visible light or near-infrared light and the second light includes a laser light.

The detecting of the first information may be performed by an absorption spectrophotometer and the detecting of the second information may be performed by a Raman spectrophotometer.

The detecting of the first information may be performed by a Fourier transform infrared spectrometer.

Each of the detecting of the first information and the detecting of the second information may further include amplifying a signal by using an attenuated total reflectance prism.

The determining of the information related to glycated hemoglobin may include determining information about a correlation of a ratio of the first extracted data and the second extracted data and a ratio of the glycated hemoglobin to the hemoglobin.

The information about the correlation may include a correlation equation or a lookup table.

Each of the extracting of the first extracted data and the extracting of the second extracted data may include extracting data of light intensity with respect to a wave number corresponding to the hemoglobin in an absorption spectrum of the first light reflected from the object and extracting data of Raman light intensity with respect to a wave number corresponding to the glucose in an absorption spectrum of the second light reflected from the object.

The method may further include directly measuring information about the glycated hemoglobin from a plurality of objects, collecting the first extracted data about the hemoglobin and the second extracted data about glucose, and obtaining a correlation of the information related to the glycated hemoglobin and a ratio of the first extracted data and the second extracted data.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Figure 1:
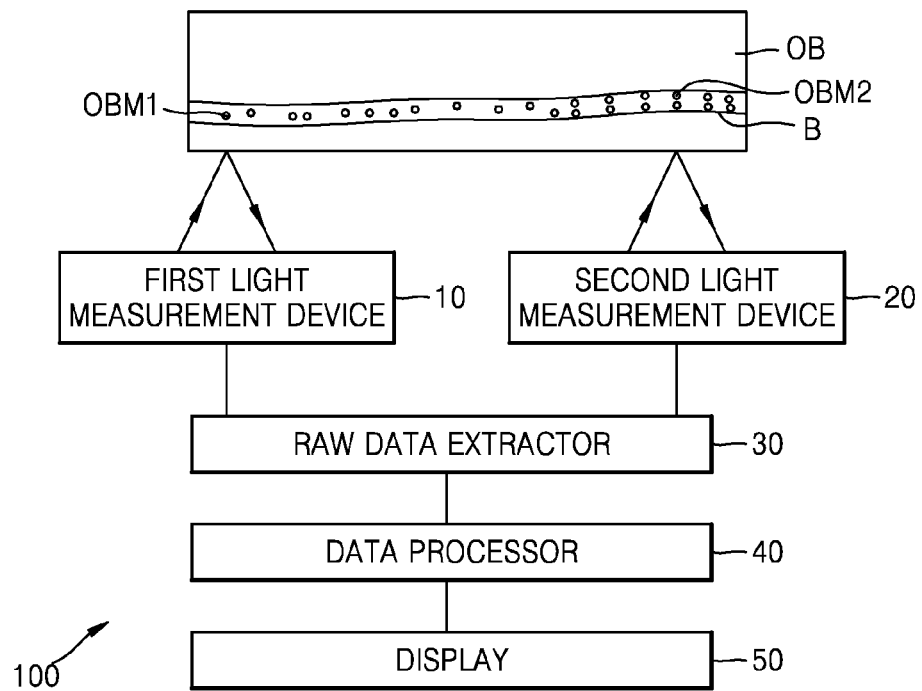
FIG. 1 schematically illustrates a noninvasive apparatus for testing glycated hemoglobin according to an exemplary embodiment.

Reference will now be made in detail to exemplary embodiments, examples of which are illustrated in the accompanying drawings, wherein like reference numerals refer to like elements throughout. Also, the thickness or size of each layer illustrated in the drawings may be exaggerated for convenience of explanation and clarity. In this regard, the exemplary embodiments may have different forms and should not be construed as being limited to the descriptions set forth herein. Accordingly, the exemplary embodiments are merely described below, by referring to the figures, to explain aspects of the inventive concept. As used herein, the term "and/or" includes any and all combinations of one or more of the associated listed items. Expressions such as "at least one of," when preceding a list of elements, modify the entire list of elements and do not modify the individual elements of the list.

FIG. 1 schematically illustrates a noninvasive apparatus 100 for testing glycated hemoglobin (HbA1c) according to an exemplary embodiment.

The noninvasive apparatus 100 for testing glycated hemoglobin may include a first light measurement device 10 radiating a first light to an object OB and detecting first information about the first light reflected from the object OB, a second light measurement device 20 radiating a second light to the object OB and detecting second information about the second light reflected from the object OB, and a data extractor 30 extracting first extracted data related to a first object material OBM1 from the first information and second extracted data related to a second object material OBM2 from the second information. The first object material OBM1 and the second object material OBM2 may exist in blood B.

The noninvasive apparatus 100 for testing glycated hemoglobin may include a data processor 40 determining information related to glycated hemoglobin from the first extracted data and the second extracted data. A display 50 may be provided to display a result of the non-invasive testing.

Figure 2:
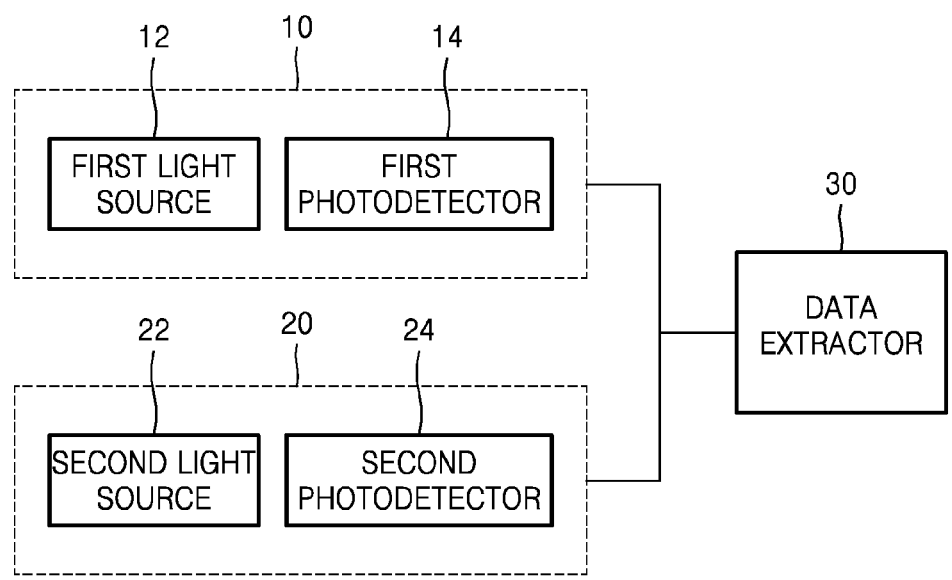
FIG. 2 is a block diagram schematically illustrating an example of a first light measurement device and a second light measurement device of the noninvasive apparatus for testing glycated hemoglobin of FIG. 1.

The object OB that is an object to be tested may be a living body, for example, a human or an animal. Referring to FIG. 2, the first light measurement device 10 may include a first light source 12 radiating the first light to the object OB and a first photodetector 14 detecting the first light reflected from the object OB. The second light measurement device 20 may include a second light source 22 radiating the second light to the object OB and a second photodetector 24 detecting the second light reflected from the object OB.

The first light may include visible light or infrared light, whereas the second light may include a laser light of a single wavelength. However, the light source is not limited thereto and may be variously selected according to the characteristics of interaction between the light and the object OB.

The first photodetector 14 may detect spectrum by splitting, for example, the first light reflected from the object OB. The first photodetector 14 may detect, for example, an absorption spectrum. The first object material OBM1 may include, for example, hemoglobin (Hb). The first photodetector 14 may include an absorption spectrophotometer that obtains the first information from the absorption spectrum. The second photodetector 24 may include, for example, a Raman spectrophotometer that obtains the second information from Raman spectrum. The Raman spectrophotometer may detect molecular information about an object material by analyzing light scattered from the object material of the object OB. The second object material OBM2 may include, for example, glucose.

The data extractor 30 may extract the first extracted data related to hemoglobin from the first information and the second extracted data related to glucose from the second information.

Figure 3:
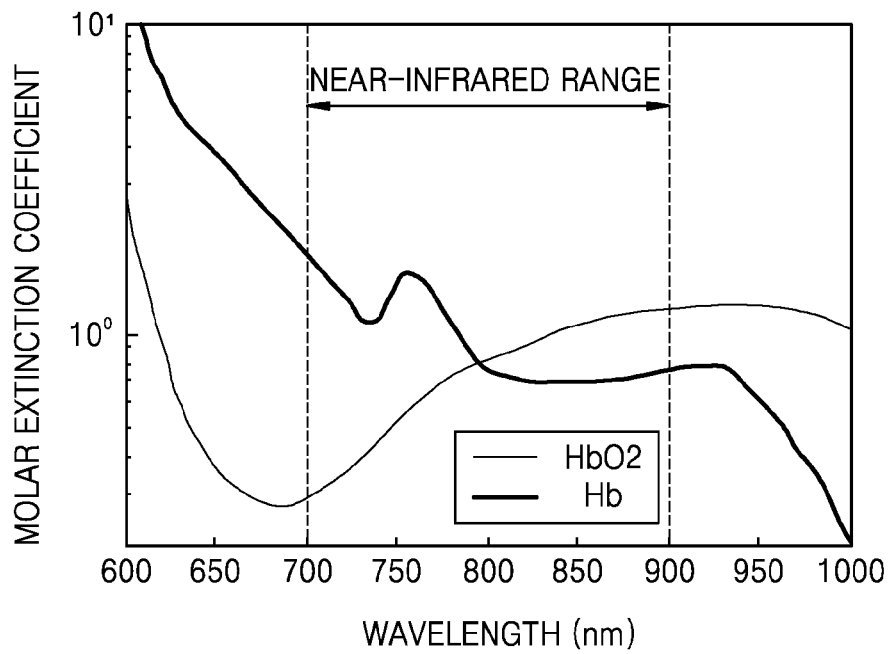
FIG. 3 is a graph showing an example of an absorption spectrum detected by a noninvasive apparatus for testing glycated hemoglobin according to an exemplary embodiment.

FIG. 3 illustrates, for example, an absorption spectrum detected by the first photodetector 14. The absorption spectrum illustrates a change of a molar extinction coefficient to a wavelength. In the absorption spectrum of FIG. 3, for example, the first information about hemoglobin in a near-infrared light range may be obtained. For example, the absorption spectrum includes a wavelength range corresponding to the hemoglobin and the first extracted data related to hemoglobin may be extracted from this wavelength range. The first extracted data may be, for example, data reflecting interaction between input light and the hemoglobin. For example, the first extracted data may be obtained from a relationship of light intensity to a wavelength or wave number of light. The data extractor may include a processor which determines the molar coefficient values received by the photodetector 14 over a relevant wavelength range, which is most pertinent to the analysis undertaken.

Absorbance with respect to an absorption wave number, or an absorption wavelength, corresponding to an object material of interest may be obtained from the absorption spectrum. In the absorption spectrum, a particular wave number, or wavelength, corresponding to an object material from which absorbance is to be obtained may be obtained by using well-known data of each material. For example, a —COOH group may have an absorption wave number of about 1740 $cm^{-1}$. A —C═O group may have an absorption wave number in a range of about 1670 $cm^{-1}$ to about 1820 $cm^{-1}$. A —C—N group may have an absorption wave number in a range of about 1080 $cm^{-1}$ to about 1360 $cm^{-1}$. For example, absorbance of the absorption wave number of the —COOH group that is one of major molecular structures of glutamate may be obtained as extracted data. Alternatively, extracted data from one of the —COOH group, the —C═O group, and the —C—N group, or a combination thereof may be obtained. Extracted data of hemoglobin may be obtained in a predetermined absorption wavelength band of a near-infrared light wavelength band of the graph of FIG. 3. For example, absorbance of a plurality of absorption wavelengths, or wave numbers, in an absorption wavelength band may be obtained as extracted data. In FIG. 3, an oxyhemoglobin ($HbO_2$) graph is illustrated as reference and extracted data may be obtained from an Hb graph. The first extracted data may include, for example, information related to hemoglobin from the absorption spectrum.

Figure 4:
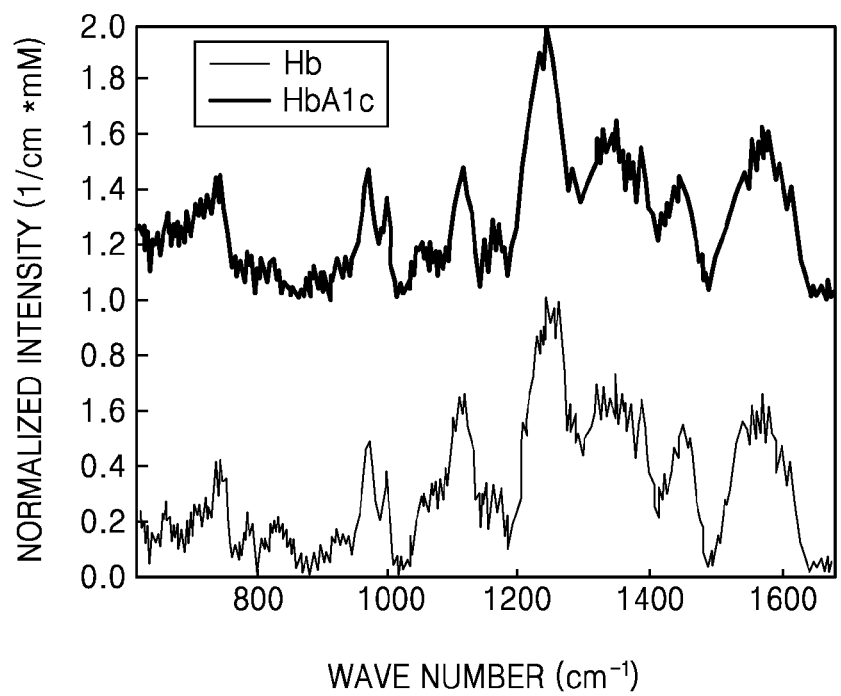
FIG. 4 is a graph showing an example of a Raman spectrum detected by a noninvasive apparatus for testing glycated hemoglobin according to an exemplary embodiment.

FIG. 4 illustrates a Raman spectrum detected by, for example, the second photodetector 24. The Raman spectrum shows a change in the light intensity with respect to a wave number, in which the light intensity may appear to be normalized. FIG. 4 illustrates a Raman spectrum of hemoglobin and a Raman spectrum of glycated hemoglobin. The second extracted data related to glycated hemoglobin may be obtained by measuring a shift value from the Raman spectrum of hemoglobin to the Raman spectrum of glycated hemoglobin. The data extractor 30 may further include a processor which determines the shift value in the Raman spectrum.

The data processor 40 may determine information about a ratio of the glycated hemoglobin to the hemoglobin from the first extracted data and the second extracted data. The data processor 40 may determine, for example, a ratio of the second extracted data to the first extracted data. The data processor 40 may include, for example, information about a first correlation between the first extracted data and a hemoglobin concentration. The hemoglobin concentration may be determined from the first extracted data by using the information about the first correlation. The data processor 40 may include, for example, information about a second correlation between the second extracted data and a glycated hemoglobin concentration. The glycated hemoglobin concentration may be determined from the second extracted data by using the information about the second correlation. A ratio of the hemoglobin concentration and the glycated hemoglobin concentration may be output from the determined glycated hemoglobin concentration and hemoglobin concentration. The data processor 40 may obtain the ratio of the hemoglobin concentration and the glycated hemoglobin concentration in other various methods.

For example, the data processor 40 may include information about a correlation between the ratio of the second extracted data to the first extracted data and the ratio of the glycated hemoglobin to the hemoglobin. The information about a correlation may be determined, for example, through the first extracted data and the second extracted data, and an algorithm to process data related to the ratio of glycated hemoglobin to hemoglobin. Once the ratio is determined, the result of the test can be output to inform a user of glycated hemoglobin level in the subject measured.

Next, an example of determining a correlation among the first and second extracted data and the information about glycated hemoglobin is described below.

Hemoglobin and glycated hemoglobin are measured by sampling blood from a plurality of objects OB. The first extracted data and the second extracted data are collected from the objects OB. For example, a first light is radiated onto the objects OB and an absorption spectrum for each of the objects OB is obtained by using an absorption spectrophotometer. Absorbance corresponding to an absorption wavelength, or an absorption wave number, of the first object material OBM1 may be obtained from each absorption spectrum. The first object material OBM1 may be, for example, at least one of molecules included in hemoglobin.

Next, a second light is radiated onto the objects OB and a Raman spectrum for each object OB is obtained by using a Raman spectrophotometer. A Raman light intensity corresponding to a Raman wavelength, or a Raman wave number, of the second object material OBM2 may be obtained from each Raman spectrum. The second object material OBM2 may be, for example, at least one of molecules included in glycated hemoglobin. For example, the second object material OBM2 may include glucose.

Next, a correlation between the ratio of the glycated hemoglobin to the measured glycated hemoglobin from the obtained blood samples and a ratio of the Raman light intensity to the second object material with respect to absorbance of the first object material OBM1 obtained from the absorption spectrum and the Raman spectrum may be determined. With the empirical measurements, the correlation may be obtained by using various algorithms. The correlation may be expressed as an equation. However, the correlation is not limited thereto and may be determined by the optical characteristics of an object material, for example, the absorbance or Raman light intensity, or a lookup table containing information related to the glycated hemoglobin, and may be determined by many other various methods.

When a correlation of the extracted data of the object material and the information about the glycated hemoglobin is obtained, the extracted data of the object material may be normalized prior to its output to the user. The absorption spectrum or Raman spectrum may be differently measured due to various factors such as a varying press force of a measurer or a change in a measured portion in each spectrum measurement. In order to reduce a deviation of spectrum, measured values may be normalized.

Figure 5:
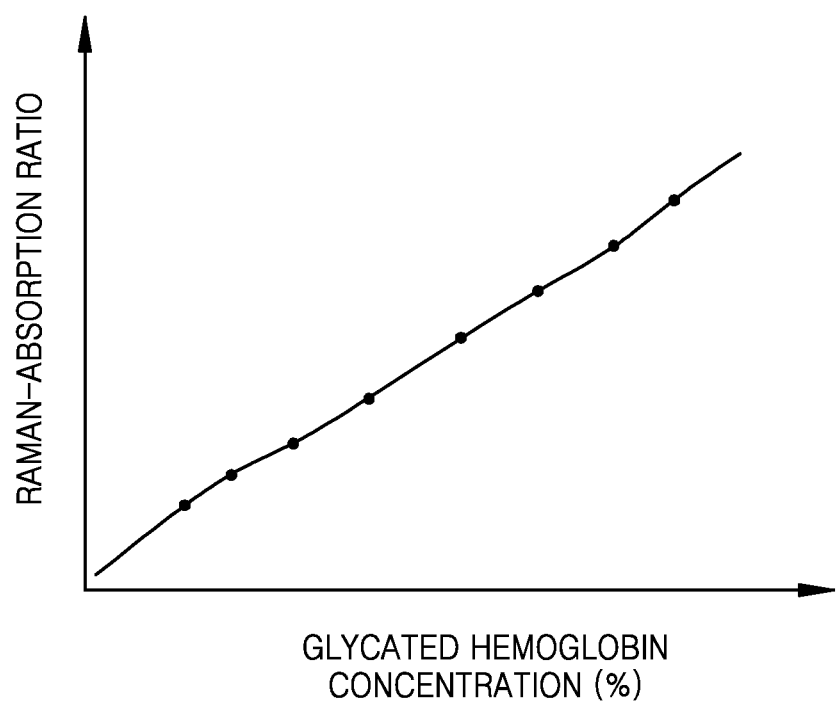
FIG. 5 is a graph showing correlation between a Raman-absorption ratio to a glycated hemoglobin concentration.

FIG. 5 is a graph showing a relationship between a ratio of a Raman light intensity to absorbance (referred to as a Raman-absorption ratio) and a glycated hemoglobin concentration. However, the illustration of FIG. 5 is exemplary for convenience of explanation. The glycated hemoglobin concentration may include, for example, a ratio of glycated hemoglobin to hemoglobin. A relationship between the ratio of a Raman light intensity to absorbance and the glycated hemoglobin concentration may be determined from the graph of FIG. 5. However, this is a mere example and the exemplary embodiments are not limited thereto. Also, an operation of obtaining a correlation between the object material and the information related to the glycated hemoglobin may be performed by the data processor 40. However, the operation may be carried out through a separate algorithm.

Diabetes tests include a blood sugar level (BSL) test, a fasting blood sugar (FBS) test, a glucose tolerance test, a glycated hemoglobin test, etc. Blood sugar signifies a concentration of glucose included in blood. A human body maintains a blood sugar level within a predetermined range to keep homeostasis. Hormones that contribute to the maintenance of a blood sugar level include glucagon, adrenaline, insulin, thyroid hormone, etc. The blood sugar level in a human body may always be maintained at about 90 mg/dl due to antagonism of the hormones. However, when en error occurs in the secretion of the hormones, a blood sugar level becomes unstable and a typical example of such a phenomenon is diabetes. Diabetes is a disease that outbreaks when the secretion of insulin of the hormones that lowers a blood sugar level malfunctions. Currently, the diabetes is treated by injecting insulin into a patient's bloodstream and/or by dietary restrictions. A concentration of glucose existing per 100 ml of blood is a blood sugar level which may be used for diagnosing diabetes, etc. A normal range of blood sugar is generally between about 70~110 mg/dl.

The glycated hemoglobin is a form of hemoglobin used to identify a glucose concentration in blood for a long period of time. The glycated hemoglobin may be formed as hemoglobin is exposed to a high blood glucose state. Human blood includes red blood cells that exist for about 120 days. As hemoglobin in red blood cells combines with glucose, glycated hemoglobin may be formed. When blood sugar of a diabetes patient is not controlled well, a level of glycated hemoglobin may increase. Since the life span of a red blood cell where glycation occurs decreases slightly, the glycated hemoglobin level may reflect an average blood sugar concentration for about three months. A normal range of a glycated hemoglobin level may be about 4%~5.9%. A certain correlation may exist between the glycated hemoglobin level and the average blood glucose concentration.

The glycated hemoglobin level may be represented as a portion of glycated hemoglobin in the entire hemoglobin by determining a ratio between glycated hemoglobin and entire hemoglobin in blood. Since the glycated hemoglobin reflects an average of blood sugars in a body for three months, the glycated hemoglobin is one of major elements in management of blood sugar, with glucose.

In an exemplary embodiment, information about glycated hemoglobin may be extracted from the extracted data of an object material obtained in a noninvasive method using light. Since a patient may take a glycated hemoglobin test in a simple manner without blood sampling, the test may be carried out without restriction to time and place and the patient may be treated according to a result of the test quickly.

Figure 6:
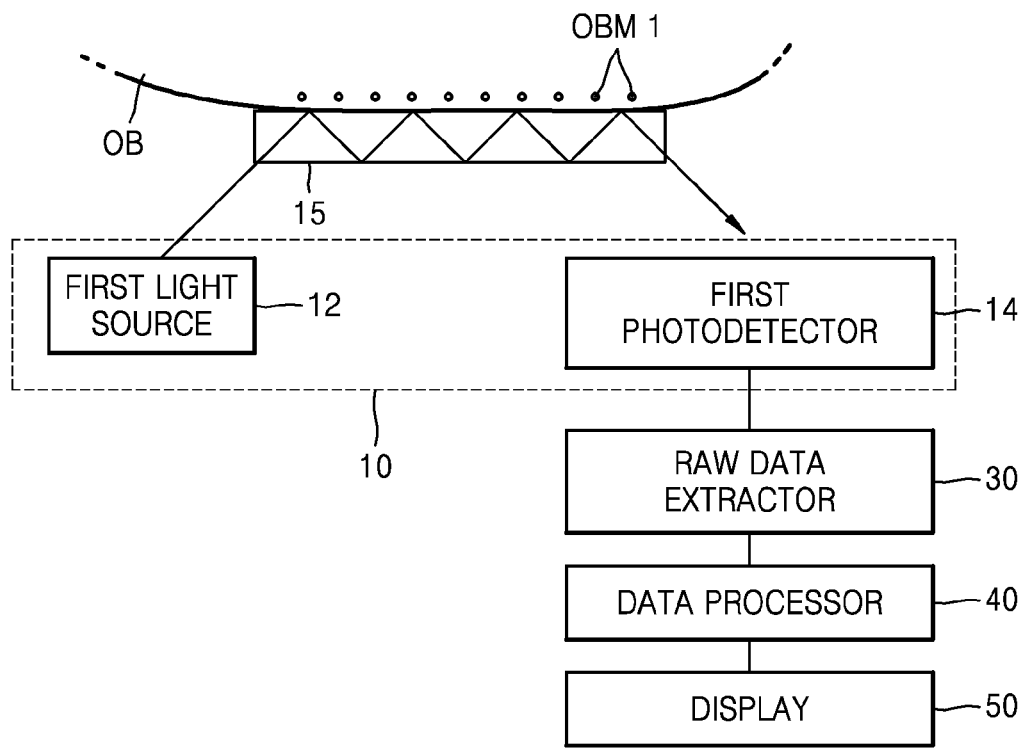
FIG. 6 schematically illustrates a noninvasive apparatus for testing glycated hemoglobin according to an exemplary embodiment.

FIG. 6 schematically illustrates an example in which an attenuated total reflectance prism 15 is further provided in the noninvasive apparatus for testing glycated hemoglobin of FIG. 1.

The attenuated total reflectance prism 15 may be arranged between the object OB and the first light measurement device 10. The attenuated total reflectance prism 15 may be arranged in contact with the object OB. An infrared spectrometer, for example, may be employed as the first photodetector 14. The attenuated total reflectance prism 15 may amplify a spectrum signal detected by the first photodetector 14 because light travels inside the attenuated total reflectance prism 15 through internal total reflection thereby increasing a reaction area with the object OB. Accordingly, the attenuated total reflectance prism 15 may enable more precise detection of the object material of the object OB. The attenuated total reflectance prism 15 may be formed of a material having a refractive index higher than that of the object OB. The attenuated total reflectance prism 15 may closely contact the object OB. For example, the attenuated total reflectance prism 15 is further provided with at least one contact sensor and thus may detect whether the attenuated total reflectance prism 15 uniformly contacts the object OB throughout the entire surface. A spectrum signal may be obtained more precisely by reflecting a result of the detection. In FIG. 6, although the attenuated total reflectance prism 15 is arranged between the object OB and the first light measurement device 10, the attenuated total reflectance prism 15 may be identically applied to the second light measurement device 20.

Figure 7:
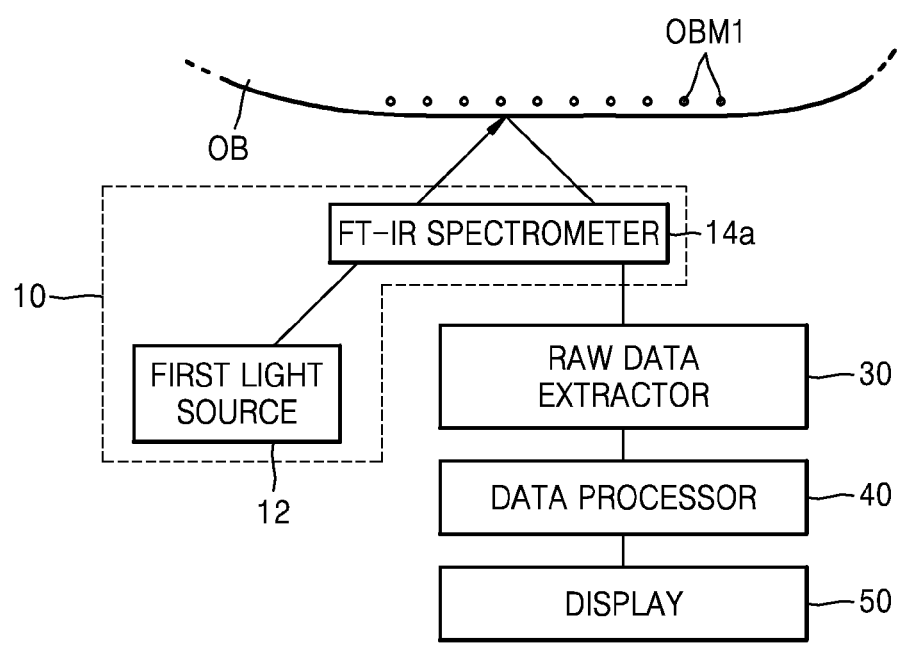
FIG. 7 schematically illustrates a noninvasive apparatus for testing glycated hemoglobin according to an exemplary embodiment.

In a noninvasive apparatus for testing glycated hemoglobin illustrated in FIG. 7, the first light measurement device 10 may include the first light source 12 and a Fourier transform infrared (FT-IR) spectrometer 14a. Compared with FIG. 2, the first photodetector 14 is changed to the FT-IR spectrometer 14a and other constituent elements may be used without a change. The FT-IR spectrometer 14a performs Fourier transform on an interference pattern obtained by using an interferometer and thus an absorption spectrum according to each wavelength may be obtained from a time domain to a frequency domain. Since the FT-IR spectrometer 14a is able to have lights of all wavelength bands simultaneously transmit through the object OB, time may be save and detection with high sensitivity may be possible as infrared light having sufficient energy is radiated.

Although it is not illustrated, in a liver function testing apparatus illustrated in FIG. 7, the attenuated total reflectance prism 15 of FIG. 6 may be further provided between the FT-IR spectrometer 14a and the object OB.

Figure 8:
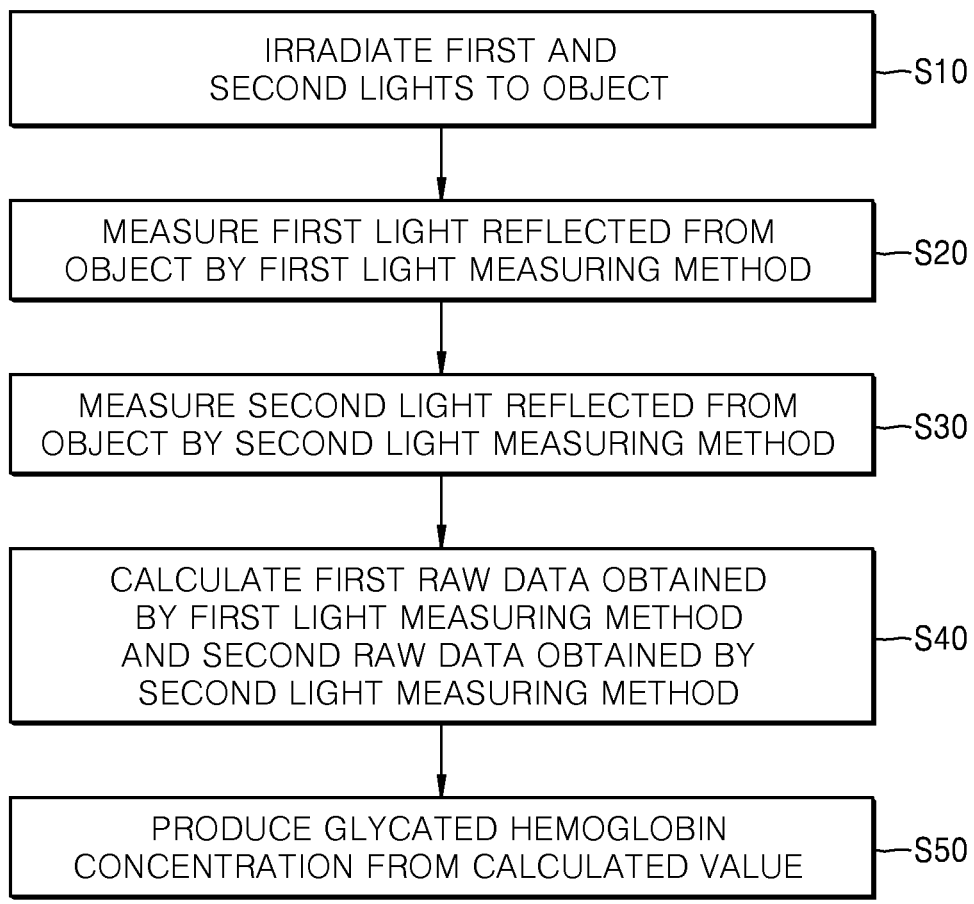
FIG. 8 is a flowchart schematically illustrating a noninvasive method for testing glycated hemoglobin according to an exemplary embodiment.

Next, a noninvasive method for testing glycated hemoglobin according to an exemplary embodiment is described in detail with reference to FIG. 8.

In the noninvasive method for testing glycated hemoglobin, a first light and a second light are radiated onto an object (S10). The first light may include, for example, visible light or infrared light. The first light reflected from the object may be measured by a first light measuring method (S20). The first light measuring method may include, for example, a spectroscopy. The first light measuring method may be performed by using, for example, absorption spectrum. The second light reflected from the object may be measured by a second light measuring method (S30). The second light measuring method may be performed by using, for example, a Raman spectrum.

The first extracted data of a first object material may be determined from a result of the first light measuring method and the second extracted data of a second object material may be determined from a result of the second light measuring method (S40). The first object material may include, for example, hemoglobin. The first extracted data may be, for example, absorbance with respect to the first object material. The second object material may include, for example, glucose. The second extracted data may be, for example, a Raman light intensity with respect to the second object material. The first extracted data and the second extracted data may be obtained. For example, a ratio of the first extracted data and the second extracted data may be determined. Information related to a glycated hemoglobin concentration may be determined from the ratio of the second extracted data to the first extracted data (S50). The information about a glycated hemoglobin concentration may include, for example, a glycated hemoglobin concentration ratio with respect to hemoglobin. The glycated hemoglobin concentration ratio with respect to hemoglobin may be extracted from a correlation with the ratio of the second extracted data to the first extracted data.

The correlation may be determined, for example, from the first extracted data and the second extracted data and through an algorithm that processes data related to the ratio of glycated hemoglobin to hemoglobin. As such, the information about glycated hemoglobin may be obtained in a noninvasive method.

Figure 9:
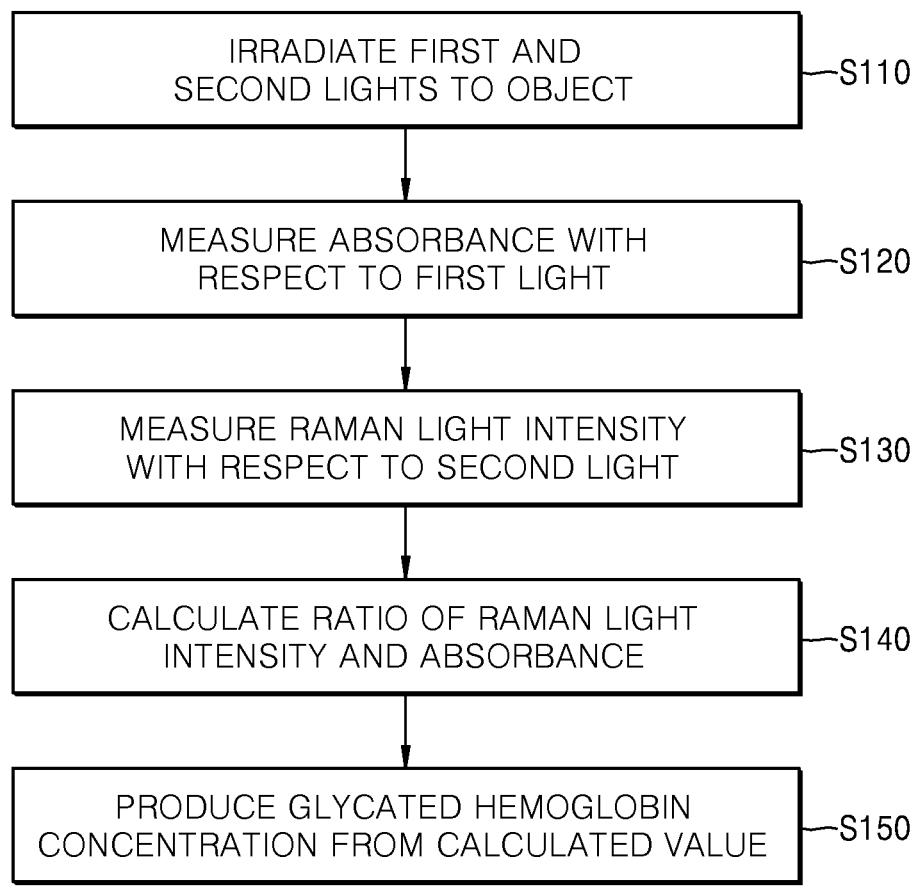
FIG. 9 is a flowchart schematically illustrating a noninvasive method for testing glycated hemoglobin according to another exemplary embodiment.

FIG. 9 illustrates a noninvasive method for testing glycated hemoglobin according to another exemplary embodiment.

A first light and a second light may be radiated onto an object (S110). The first light may include, for example, visible light and infrared light. The second light may include a laser light.

Absorbance is measured with respect to the first light (S120). For example, absorbance of the first light may be measured as absorbance of an absorption wavelength or an absorption wave number corresponding to a first object material. The first object material may include, for example, hemoglobin. A Raman light intensity may be measured with respect to the second light (S130). The Raman light intensity may include the intensity of light scattered in the object. The Raman light intensity may include information about a second object material. The second object material may include, for example, glucose. The second object material may include, for example, glucose bonded to an end of β-chain of hemoglobin. Next, a ratio of a Raman light intensity and absorbance may be determined (S140). In other words, a ratio of a Raman light intensity to absorbance may be determined. Information about a glycated hemoglobin concentration may be determined from the ratio of a Raman light intensity to absorbance (S150).

The information about a glycated hemoglobin concentration may include, for example, the glycated hemoglobin concentration ratio with respect to hemoglobin. The glycated hemoglobin concentration ratio with respect to hemoglobin may be extracted from a correlation from the ratio of a Raman light intensity to absorbance.

The correlation may be determined, for example, from the absorbance and the Raman light intensity, and through an algorithm that processes data related to a ratio of glycated hemoglobin to hemoglobin. As such, the information about glycated hemoglobin may be measured in a noninvasive method.

As described above, in the noninvasive method for testing glycated hemoglobin according to the above-described exemplary embodiment, since glycated hemoglobin may be simply tested in a noninvasive method without sampling blood from an object, the method may be conveniently used by a user. Also, since a user may frequently check a glycated hemoglobin level by oneself, the method may be helpful for a health management. Also, in the noninvasive apparatus for testing glycated hemoglobin according to the above-described exemplary embodiment, the apparatus may be employed in mobile devices, and a result of a glycated hemoglobin test directly performed by a user may be displayed through a mobile display. Also, the test result may be transmitted from the mobile device to a server of a hospital used by the user and thus user's health management may be achieved through bi-directional communications.

It should be understood that exemplary embodiments described herein should be considered in a descriptive sense only and not for purposes of limitation. Descriptions of features or aspects within each embodiment should typically be considered as available for other similar features or aspects in other embodiments.

While one or more embodiments of the present inventive concept have been described with reference to the figures, it will be understood by those of ordinary skill in the art that various changes in form and details may be made therein without departing from the spirit and scope of the present inventive concept as defined by the following claims and their equivalents.

What is claimed is:

1. An apparatus for non-invasively testing glycated hemoglobin, the apparatus comprising:
    a first light measurement device configured to radiate a first light to an object and detect first information about the first light reflected from the object;
    a second light measurement device configured to radiate a second light to the object and detect second information about the second light reflected from the object;
    a data extractor configured to extract first extracted data related to an amount of hemoglobin from the first information and second extracted data related to an amount of glucose from the second information; and
    a data processor configured to determine information related to a concentration of glycated hemoglobin in the object from the first extracted data and the second extracted data.

2. The apparatus of claim 1, further comprising a display configured to output the information related to the concentration of glycated hemoglobin as a result of a test performed on the object for use in health management based on the concentration of glycated hemoglobin.

3. The apparatus of claim 1, wherein the data extractor is further configured to determine a ratio of the second extracted data to the first extracted data, wherein the first extracted data is compared to an extinction coefficient of a reference material to obtain the amount of the hemoglobin.

4. The apparatus of claim 3, wherein the data processor is further configured to determine a ratio of the glycated hemoglobin to the hemoglobin from the first extracted data and the second extracted data.

5. The apparatus of claim 1, wherein the first light comprises visible light or near-infrared light, and the second light comprises a laser light, and wherein the concentration of glycated hemoglobin represents an average blood sugar level over a period of weeks.

6. The apparatus of claim 1, wherein the first light measurement device comprises an absorption spectrophotometer and the second light measurement device comprises a Raman spectrophotometer.

7. The apparatus of claim 6, wherein the first light measurement device comprises a Fourier transform infrared spectrometer.

8. The apparatus of claim 1, wherein each of the first light measurement device and the second light measurement device comprises an attenuated total reflectance prism.

9. The apparatus of claim 1, wherein the data processor is further configured to determine information about a correlation of a ratio of the first extracted data and the second extracted data and a ratio of the glycated hemoglobin to the hemoglobin.

10. The apparatus of claim 9, wherein the information about the correlation comprises a correlation equation or a lookup table.

11. The apparatus of claim 1, wherein the data extractor is configured to extract data of light intensity with respect to a wave number corresponding to the hemoglobin in an absorption spectrum of the first light reflected from the object, and data of Raman light intensity with respect to a wave number corresponding to the glucose in an absorption spectrum of the second light reflected from the object.

12. A method for non-invasively testing glycated hemoglobin, the method comprising:
    radiating a first light to an object;
    radiating a second light to the object;
    detecting first information about the first light reflected from the object;
    detecting second information about the second light reflected from the object;
    extracting first extracted data related to an amount of hemoglobin from the first information;
    extracting second extracted data related to and amount of glucose from the second information; and
    determining information related to a concentration of glycated hemoglobin in the object from the first extracted data and the second extracted data.

13. The method of claim 12, further comprising displaying the information related to the concentration of glycated hemoglobin as a result of a test performed on the object for use in health management based on the concentration of glycated hemoglobin.

14. The method of claim 12, further comprising determining a ratio of the second extracted data to the first extracted data, wherein the first extracted data is compared to an extinction coefficient of a reference material to obtain the amount of the hemoglobin.

15. The method of claim 14, wherein the determining the information related to glycated hemoglobin comprises determining a ratio of the glycated hemoglobin to the hemoglobin from the first extracted data and the second extracted data.

16. The method of claim 12, wherein the first light comprises visible light or near-infrared light and the second light comprises a laser light, and wherein the concentration of glycated hemoglobin represents an average blood sugar level over a period of weeks.

17. The method of claim 12, wherein the detecting the first information is performed by an absorption spectrophotometer and the detecting the second information is performed by a Raman spectrophotometer.

18. The method of claim 17, wherein the detecting the first information is performed by a Fourier transform infrared spectrometer.

19. The method of claim 12, wherein each of the detecting the first information and the detecting the second information comprises amplifying a signal by using an attenuated total reflectance prism.

20. The method of claim 12, wherein the determining of the information related to glycated hemoglobin comprises determining information about a correlation of a ratio of the first extracted data and the second extracted data and a ratio of the glycated hemoglobin to the hemoglobin.

21. The method of claim 20, wherein the information about the correlation comprises a correlation equation or a lookup table.

22. The method of claim 12, wherein each of the extracting the first extracted data and the extracting the second extracted data comprises extracting data of light intensity with respect to a wave number corresponding to the hemoglobin in an absorption spectrum of the first light reflected from the object and extracting data of Raman light intensity with respect to a wave number corresponding to the glucose in an absorption spectrum of the second light reflected from the object.

23. The method of claim 12, further comprising:
    non-invasively measuring information about the glycated hemoglobin from a plurality of objects;
    collecting the first extracted data about the hemoglobin and the second extracted data about glucose; and
    obtaining a correlation of the information related to the glycated hemoglobin and a ratio of the first extracted data and the second extracted data.

* * * * *